United States Patent [19]
Roberts et al.

[11] Patent Number: 5,997,715
[45] Date of Patent: Dec. 7, 1999

[54] METHOD OF ELECTROCHEMICALLY PRODUCING EPOXIDES

[75] Inventors: David G. Roberts, Gibsonia; Peter C. Foller, Murrysville; Robert H. Tang, Murrysville; Yingchao Zhang, Murrysville; James R. Franks, Gibsonia, all of Pa.

[73] Assignee: PPG Industries Ohio, Inc., Cleveland, Ohio

[21] Appl. No.: 09/112,659

[22] Filed: Jul. 9, 1998

[51] Int. Cl.[6] ................................................. C25B 3/00
[52] U.S. Cl. ............................................. 205/428; 205/456
[58] Field of Search ....................................... 205/428, 456

[56] References Cited

U.S. PATENT DOCUMENTS

| | | | |
|---|---|---|---|
| 3,288,692 | 11/1966 | Le Duc | 204/80 |
| 3,351,635 | 11/1967 | Kollar | 260/348.5 |
| 3,427,235 | 2/1969 | Le Duc | 204/78 |
| 3,451,905 | 6/1969 | Krönig et al. | 204/80 |
| 3,501,388 | 3/1970 | Krönig et al. | 204/79 |
| 3,635,803 | 1/1972 | Binns et al. | 204/80 |
| 4,560,451 | 12/1985 | Nielsen | 204/79 |
| 4,634,506 | 1/1987 | Novak et al. | 204/80 |
| 4,726,887 | 2/1988 | McIntyre | 204/80 |
| 5,411,641 | 5/1995 | Trainham, III et al. | 204/59 R |
| 5,527,436 | 6/1996 | Cooker et al. | 204/428 |
| 5,900,133 | 5/1999 | Foller et al. | 205/551 |

FOREIGN PATENT DOCUMENTS

| | | |
|---|---|---|
| 637691 | 3/1964 | Belgium . |
| 1258856 | 1/1968 | Germany . |
| 1090006 | 11/1967 | United Kingdom . |

OTHER PUBLICATIONS

Holbrook et al., "Electrooxidation of Olefins at a Silver Electrode", *Journal of Catalysis* 1975, vol. 38, pp. 294–298. no month available.

Chou et al., "Anodic Oxidation of Propylene on a Screen Electrode", *Chemical Engineering Science* 1980, vol. 35, pp. 1581–1590. no month available.

Van Der Eijk et al., "Electrochemical Epoxidation of Olefins", *Catalysis Today* 1988, vol. 3, pp. 259–266. no month available.

Scott et al., Pilot Scale Electrosynthesis of Alkene Oxides by Direct and Indirect Oxidation in a Sieve Plate Electrochemical Reactor, *Chemical Engineering Science* 1992, vol. 47, pp. 2957–2962. no month available.

Oduoza et al., Aspects of the Direct Electrochemical Oxidation of Propylene, *Chem. Eng. Symp. Series* 1994, No. 127, pp. 37–47. no month available.

Otsuka et al., Simultaneous Epoxidation of 1–Hexene and Hydroxylation of Benzene During Electrolysis of Water, *Chemistry Letters* 1994, pp. 1861–1864. no month available.

Otsuka et al., Electrocatalytic Synthesis of Propylene Oxide During Water Electrolysis, *Journal of Catalysis* 1995, vol. 157, pp. 450–460. no month available.

*Primary Examiner*—Kathryn Gorgos
*Assistant Examiner*—Edna Wong
*Attorney, Agent, or Firm*—James R. Franks; Irwin M. Stein

[57] ABSTRACT

Describes a method of electrochemically converting α-halohydrins, e.g., 1-chloro-2-hydroxypropane and 1,3-dichloro-2-hydroxypropane, to epoxides, e.g., propylene oxide and epichlorohydrin. A three compartment electrolytic cell is provided having (1) a catholyte compartment containing a cathode assembly comprising a cathode and anion exchange membrane, (2) an anolyte compartment containing an anode assembly comprising an anode and a cation exchange membrane, and (3) an intermediate compartment partitioned from the catholyte and anolyte compartments by the anion and cation exchange membranes respectively. An aqueous solution of α-halohydrin is charged to the catholyte compartment, while hydrogen halide solutions are charged to the intermediate and anolyte compartments. Direct current is passed through the electrolytic cell and an aqueous solution comprising epoxide is removed from the catholyte compartment.

18 Claims, 3 Drawing Sheets

METHOD OF ELECTROCHEMICALLY PRODUCING EPOXIDES

DESCRIPTION OF THE INVENTION

The present invention relates to a method of electrochemically producing epoxides, e.g., alkylene oxides and epihalohydrins. Particularly, the present invention relates to an electrochemical method of converting α-halohydrins to epoxides. The present invention also relates to the use of electrolytic cells having an intermediate compartment partitioned from a catholyte compartment by an anion exchange membrane and from an anolyte compartment by a cation exchange membrane.

Commercial methods of producing epoxides, such as alkylene oxides include, for example: vapor phase oxidation of alkylene, e.g., ethylene, with molecular oxygen in the presence of a silver catalyst; catalytic reaction of alkylene, e.g., propylene, with an organic hydroperoxide, as described in U.S. Pat. No. 3,351,635; and what is known in the art as the halohydrin process. The halohydrin process, e.g., chlorohydrin process, is among the most common commercial methods of producing alkylene oxide, e.g., propylene oxide. The production of propylene oxide by the chlorohydrin process typically comprises three steps, chlorohydrination, dehydrochlorination, i.e., epoxidation, and product separation.

Chlorohydrination involves the reaction of propylene with chlorine in aqueous solution to form two isomers of propylene chlorohydrin. In the dehydrochlorination step, alkali metal hydroxide, such as sodium hydroxide, or milk of lime is added to the aqueous propylene chlorohydrin solution to form an aqueous solution of propylene oxide, organic co-products and brine, e.g., an aqueous salt solution such as aqueous sodium chloride. Separation of propylene oxide and organic co-products from the brine typically involves an evaporative or distillation process. Propylene oxide is usually separated from the organic co-products by fractional distillation. The presence of halide anion, e.g., chloride anion, in the brine requires that the distillation column(s) be fabricated from expensive corrosion resistant materials, such as titanium and stainless steel. Moreover, the waste water resulting from the distillation process is typically treated prior to disposal to remove trace amounts of organic compounds.

In the most common process of manufacturing epichlorohydrin, allyl chloride is reacted with chlorine in aqueous solution to give a mixture of 1,2-dichloro-3-propanol and 1,3-dichloro-2-propanol, sometimes referred to as an isomeric mixture of glycerol chlorohydrins. This isomeric mixture is dehydrochlorinated with an alkali and the resulting epichlorohydrin separated by steam stripping. Final purification can be accomplished by distillation. As with the above described chlorohydrin process, distillation column(s) are typically fabricated from expensive corrosion resistant materials, and the distillation waste water treated prior to disposal. In addition, contact times in all steps must be carefully controlled to minimize hydrolysis of the epichlorohydrin.

The commercial methods described above can be expensive, particularly with regard to the cost of distillation equipment, utility costs, raw material costs and the required treatment of waste streams. As a result, such methods are dedicated typically to the high volume production of epoxides and can be expensive to expand.

Methods of electrochemically producing alkylene oxide, which utilize a variety of electrochemical cell configurations and feed streams have been described in, for example, U.S. Pat. Nos. 3,288,692; 3,427,235; 3,451,905; 3,501,388; 3,635,803; 4,560,451; 4,634,506; 4,726,887; and 5,527,436. The described electrochemical cell configurations include, single compartment, two compartment and bipolar stacked arrays. The described feed streams include, water, oxygen, alkali metal halide, e.g., potassium bromide, and olefin, e.g., propylene.

Because of the drawbacks of current commercial methods, alternative methods for producing epoxides, e.g., alkylene oxides such as propylene oxide, that are lower in cost with regard to capital investment for equipment, raw material costs, and costs for the treatment of waste streams are continually being sought. In accordance with an embodiment of the present invention, a method of converting α-halohydrins to epoxides, e.g., alkylene oxide, is provided, said method comprising:

(a) providing an electrolytic cell having a catholyte compartment containing a cathode assembly, an anolyte compartment containing an anode assembly, and an intermediate compartment separating said catholyte and anolyte compartments;

(b) introducing an aqueous solution of α-halohydrin into said catholyte compartment;

(c) introducing a first aqueous solution comprising hydrogen halide into said intermediate compartment;

(d) introducing a second aqueous solution comprising hydrogen halide into said anolyte compartment;

(e) passing direct current through said electrolytic cell; and (f) removing an aqueous solution comprising an epoxide from said catholyte compartment, said cathode assembly comprising a cathode and an anion exchange membrane, said anode assembly comprising a cation exchange membrane and an anode, and said intermediate compartment being partitioned from said catholyte and anolyte compartments respectively by said anion exchange membrane and said cation exchange membrane.

In accordance with a further embodiment of the present invention, there is provided a method of converting α-halohydrin to an epoxide as described above, wherein steps (c) and (d) are replaced with a single step in which an aqueous solution comprising hydrogen halide is circulated through both of the anolyte and intermediate compartments.

The features that characterize the present invention are pointed out with particularity in the claims, which are annexed to and form a part of this disclosure. These and other features of the invention, its operating advantages and the specific objects obtained by its use will be more fully understood from the following detailed description and the accompanying drawings in which preferred embodiments of the invention are illustrated and described.

Other than in the operating examples, or where otherwise indicated, all numbers expressing quantities of ingredients, reaction conditions, and so forth used in the specification and claims are to be understood as modified in all instances by the term "about".

BRIEF DESCRIPTION OF THE DRAWINGS

In FIGS. 1–3, like reference numerals represent the same structural parts, the same process streams and the same conduits.

DETAILED DESCRIPTION OF THE INVENTION

Figure 1:
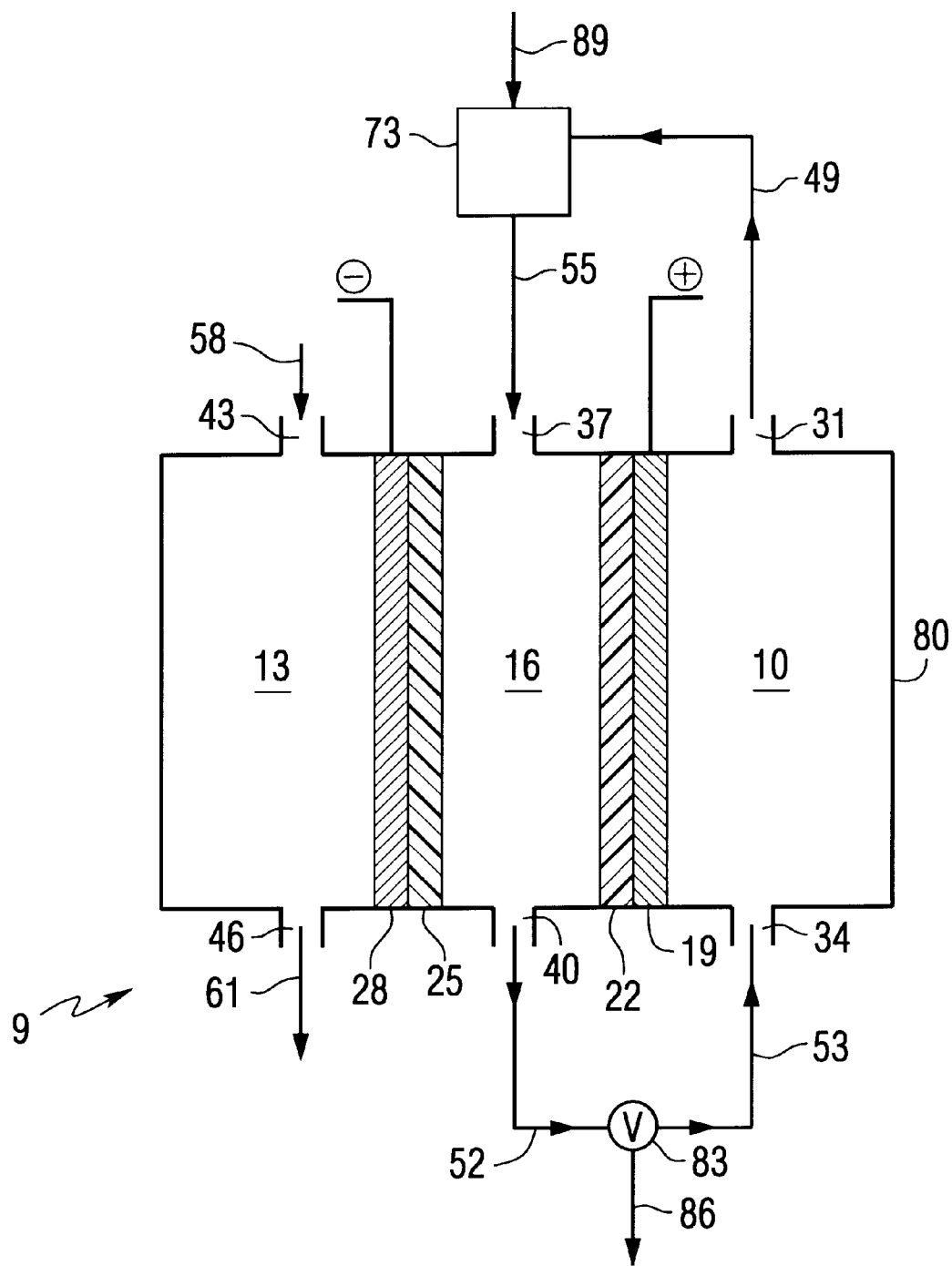
FIG. 1 is a schematic representation of an electrolytic cell useful for converting α-halohydrin to an epoxide in accordance with the method of the present invention.
Figure 2:
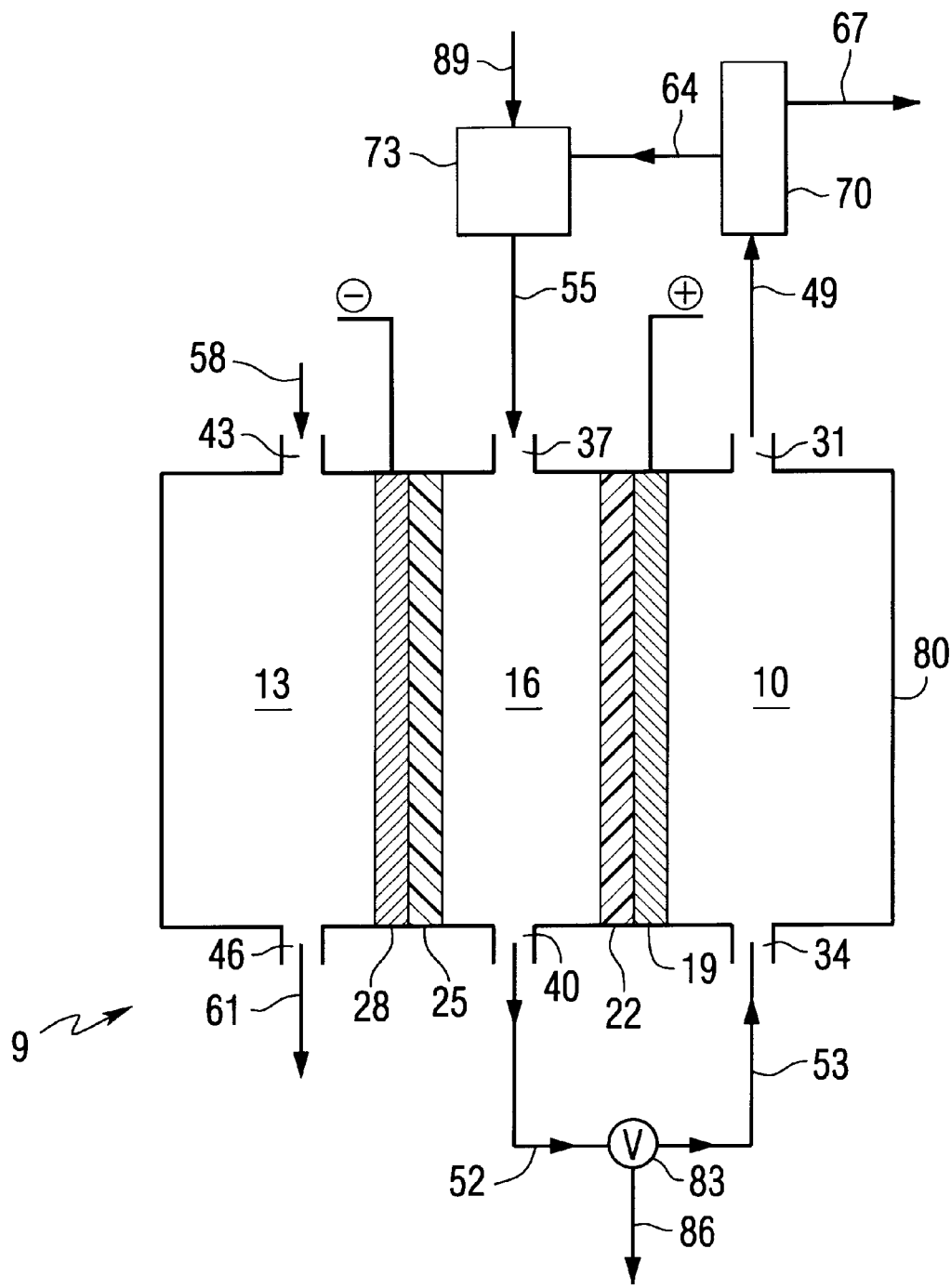
FIG. 2 is a schematic representation of the electrolytic cell of FIG. 1 further comprising a liquid-gas separator as part of the liquid communication closed loop around the anolyte and intermediate compartments.
Figure 3:
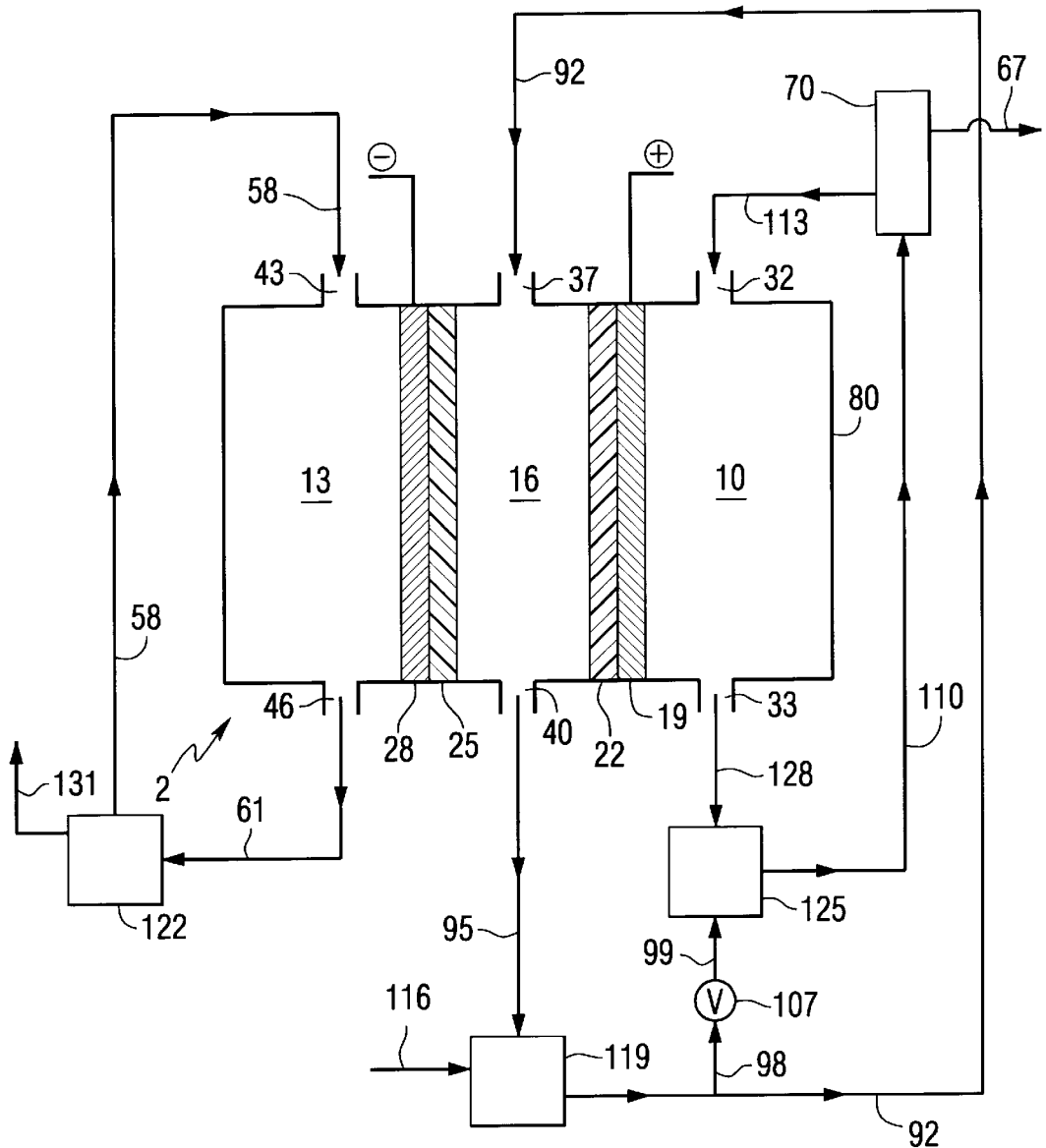
FIG. 3 is a schematic representation of an electrolytic cell similar to that of FIG. 1 having separate liquid communication closed loops around each of the intermediate and anolyte compartments and wherein a portion of the process stream removed from the intermediate compartment may be introduced into the anolyte compartment.

In the practice of the present invention, electrolytic cells, such as those represented in FIGS. 1 through 3, are provided for the production of epoxides from α-halohydrins. Referring now to FIG. 3, electrolytic cell 2 comprises a housing 80 having therein a catholyte compartment 13, an anolyte compartment 10, and an intermediate compartment 16. Catholyte compartment 13 has an inlet 43, an outlet 46, and also has therein a cathode assembly comprising a cathode 28, which is substantially rigid and provides support for anion exchange membrane 25. Anolyte compartment 10 has an inlet 32, an outlet 33, and also has therein an anode assembly comprised of anode 19, which is substantially rigid and provides support for cation exchange membrane 22. Intermediate compartment 16 has an inlet 37 and an outlet 40, and is partitioned from catholyte compartment 13 by anion exchange membrane 25, more particularly, the cathode assembly, and is separated from anolyte compartment 10 by cation exchange membrane 22, more particularly, the anode assembly.

FIGS. 1 and 2 depict electrolytic cell 9 in which intermediate compartment 16 and anolyte compartment 10 are in liquid communication by means of a closed loop. In FIG. 1, outlet 40 of intermediate compartment 16 is shown in liquid communication with inlet 34 of anolyte compartment 10 by conduits (as shown by lines 52 and 53) connected to valve 83. Outlet 31 of anolyte compartment 10 and inlet 37 of intermediate compartment 16 are shown in liquid communication through reservoir 73 by way of conduits (shown by lines 49 and 55).

Electrolytic cells 9 and 2 may be assembled by any appropriate method as long as the basic structural arrangements of component parts, as depicted in FIGS. 1–3, are maintained. For example, the catholyte, anolyte, and intermediate compartments may each be fabricated separately and then assembled by clamping or otherwise fastening the compartments together.

Housing 80 may be fabricated from any of the known conventional materials for electrolytic cells, or combinations of these known materials, that are preferably at least corrosion resistant to and compatible with the materials being circulated through the catholyte, anolyte and intermediate compartments or materials formed in these compartments. Examples of materials from which housing 80 may be fabricated include, but are not limited to: metal, e.g., stainless steel, titanium and nickel; plastics, e.g., polytetrafluoroethylene, which is sold under the trademark TEFLON and which is commercially available from E.I. du Pont de Nemours and Company, poly(vinylidene fluoride), glass filled polytetrafluoroethylene, polypropylene, poly(vinyl chloride), chlorinated poly(vinyl chloride) and high density polyethylene. Preferred materials from which housing 80 may be fabricated include poly(vinylidene fluoride) and stainless steel.

If housing 80 is fabricated from an electrically conductive material, such as stainless steel, then appropriately positioned nonconductive gaskets would typically also be present, as is known to those of ordinary skill in the art. For example, if the various compartments of the cell are prefabricated separately from stainless steel, such gaskets would typically be placed between those portions of the prefabricated compartments that would otherwise abut each other upon assembly of the electrolytic cell. Such nonconductive gaskets may be fabricated from synthetic polymeric materials, e.g., copolymers of ethylene and propylene, and fluorinated polymers.

Cathode 28 and anode 19 may each be fabricated from any appropriate material that is at least both corrosion resistant to the environments to which they are exposed and electrically conductive. It is also desirable that cathode 28 and anode 19 each be substantially rigid so as to provide support for, respectively, anion exchange membrane 25 and cation exchange membrane 22. Materials from which cathode 28 may be fabricated include, but are not limited to: graphite, platinum, titanium coated with platinum, titanium coated with an oxide of ruthenium, nickel, stainless steel, specialty steels including high alloy steels containing nickel, chromium, and molybdenum, e.g., HASTELLOY® C-2000™ alloy and HASTELLOY® C-276™ alloy from Haynes International, Inc.

In the practice of the present invention, it is preferred that anode 19 be fabricated from a material(s) that provides a catalytic surface upon which halide anions, e.g., chloride anions, are electrochemically oxidized to form diatomic halogen, e.g., diatomic chlorine ($Cl_2$), to the substantial exclusion of the electrochemical oxidation of water to form diatomic oxygen and protons. An example of a class of anode that may be used in the present invention is referred to in the art as a "dimensionally stable anode" (DSA). A particularly preferred combination of materials from which anode 19 can be fabricated are titanium and oxides of ruthenium, more particularly, titanium coated with an oxide of ruthenium. Such ruthenium oxide coated titanium anodes are available commercially from Electrode Corporation and De Nora Permelec S.P.A.

Preferably, both cathode 28 and anode 19 have a perforated or mesh-like configuration. A perforated or mesh-like configuration provides for increased electrode, i.e., cathode and anode, surface area, and minimizes interference with the transport of ions across the anion and cation exchange membranes.

The anion exchange membrane 25 used in the practice of the present invention may be prepared from any appropriate material that is permeable to and capable of transferring anions. Typically, such anion exchange membranes are prepared from commercially available organic polymers, often thermoplastic polymers, containing weakly basic pendant polar groups. The anionic membrane may comprise polymers based on fluorocarbons, polystyrene, polypropylene, polybutadiene, polyisoprene, polyisobutylene, polyethylene and hydrogenated styrene/butadiene block copolymers. For example, one such representative anion exchange membrane comprises polystyrene which has dialkylamino groups that have been converted into quaternary ammonium ions covalently bonded to at least some of the benzene rings of the polystyrene backbone. It is preferable that the anion exchange membrane also be physically durable and stable towards exposure to acids, in particular hydrogen halides, e.g., hydrogen chloride.

A particular example of an anion exchange membrane used in the practice of the present invention is a copolymer of styrene and divinylbenzene which contains from 4 percent (%) to 16%, typically from 6% to 8%, by weight of divinylbenzene and also quaternary ammonium groups as anion carriers. Such membranes are available commercially under the trade designation RAIPORE® from RAI Research Corporation, and TOSFLEX® from Tosoh Corporation. Other suitable membranes include, but are not limited to: NEOSEPTA® membranes from Tokuyama Soda, SELEMION membranes from Asahi Glass, and IONAC MA 3148, MA 3236 and MA 3457 membranes (based on a polymer of heterogeneous poly(vinyl chloride) substituted with quaternary ammonium groups) from Ritter-Pfaulder Corporation. Particularly preferred anion exchange membranes are NEOSEPTA® ACM and NEOSEPTA® AHA-2 membranes (available commercially from Tokuyama Soda of Japan) which are described as being comprised of a copolymer of styrene and divinylbenzene having pendent quaternary ammonium groups.

Cation exchange membrane 22 used in the practice of the present invention may be prepared from any appropriate material that is permeable to and capable of transferring cations. Examples of classes of materials that may comprise the cation exchange membrane include, but are not limited to, organic polymers, in particular synthetic organic polymers, and ceramics, e.g., beta-alumina. The use of synthetic organic polymers having pendent acidic groups is preferred, many of which are commercially available or can be made according to art-recognized methods. A preferred class of synthetic organic polymers are fluoropolymers, more preferably perfluoropolymers, and in particular copolymers comprised of two or more fluoromonomers or perfluoromonomers, having pendent acid groups, preferably pendent sulfonic acid groups.

When cation exchange membrane 22 is fabricated from fluorinated polymer(s) or copolymer(s), the pendent acid groups may include the following representative general formulas: $—CF_2CF(R)SO_3H$; and $—OCF_2CF_2CF_2SO_3H$, where R is a F, Cl, $CF_2Cl$, or a $C_1$ to $C_{10}$ perfluoroalkyl radical. The synthetic organic polymer of the cation exchange membrane may, for example, be a copolymer of ethylene and a perfluorinated monomer, as represented by the following general formula, $CF_2=CFOCF_2CF(CF_3)OCF_2CF_2SO_3H$. These copolymers may have pendent sulfonyl fluoride groups ($—SO_2F$), rather than pendent sulfonic acid groups ($—SO_3H$). The sulfonyl fluoride groups ($—SO_2F$) can be reacted with potassium hydroxide to form $—SO_3K$ groups, which can then be reacted with an acid to form sulfonic acid groups $—SO_3H$.

Suitable cation exchange membranes comprising copolymers of polytetrafluoroethylene and poly(vinyl ether) containing pendant sulfonic acid groups are offered by E.I. du Pont de Nemours and Company under the trademark "NAFION" (hereinafter referred to as NAFION®). In particular, NAFION® membranes containing pendant sulfonic acid groups include NAFION® 117, NAFION® 324 and NAFION® 417 membranes. The NAFION® 117 membrane is described as an unsupported membrane having an equivalent weight of 1100 grams per equivalent (g/eq), equivalent weight being here defined as that amount of resin required to neutralize one liter of a 1 Molar (M) sodium hydroxide solution. The NAFION® 324 and NAFION® 417 membranes are described as being supported on a fluorocarbon fabric. The NAFION® 417 membrane has an equivalent weight of 1100 g/eq. The NAFION® 324 membrane is further described as having a two-layer structure comprised of: a 125 micrometer ($\mu$m) thick membrane having an equivalent weight of 1100 g/eq; and a 25 $\mu$m thick membrane having an equivalent weight of 1500 g/eq.

While the use of cation exchange membranes based on synthetic organic polymers are preferred, it is within the scope of the practice of the method of the present invention to use other cation-transporting membranes which are not polymeric. For example, solid state proton conducting ceramics such as beta-alumina may be used. Examples of representative solid proton conductors that may be used are listed in columns 6 and 7 of U.S. Pat. No. 5,411,641, which disclosure is incorporated herein by reference.

Within the catholyte and anolyte compartments of electrolytic cells 9 and 2, the cathode and anode assemblies are held together by any appropriate means. Such methods include, but are not limited to: maintaining a higher internal pressure within intermediate compartment 16 relative to catholyte compartment 13 and anolyte compartment 10; clamping components, 28 and 25, and 22 and 19 together; providing a biasing element within at least intermediate compartment 16, e.g., an electrically nonconductive plastic spring, not shown, can be placed within intermediate compartment 16 such that is in biased contact with anion exchange membrane 25 and cation exchange membrane 22; and combinations of these methods.

Maintaining the ion exchange membranes and the electrodes of the electrode assemblies in close contact with each other serves to enhance the operating efficiency of the electrolytic cells used in the current invention. For example, as ions are electrochemically formed or consumed at the electrodes, close proximity, i.e., close or abutting contact, of the ion exchange membranes thereto results in improved ion transport across the membranes. However, it is contemplated that the electrodes not be in close proximity to their respective ion exchange membranes, i.e., being positioned elsewhere in the catholyte or anolyte compartments respectively.

In a preferred embodiment of the present invention, anion exchange membrane 25 and cation exchange membrane 22 are maintained in contact with cathode 28 and anode 19 respectively by a positive internal pressure differential between intermediate compartment 16 and each of catholyte compartment 13 and anolyte compartment 10. By positive internal pressure differential is here meant that intermediate compartment 16 has an internal pressure greater than that of each of catholyte compartment 13 and anolyte compartment 10. For example, the positive internal pressure differential value between the intermediate and anolyte compartments is determined by subtracting the internal pressure of anolyte compartment 10 from that of intermediate compartment 16.

The upper limit of the positive internal pressure differential between intermediate compartment 16 and each of the catholyte and anolyte compartments will depend on a number of factors including, for example, the maximum pressure that the anion and cation exchange membranes can each resist before they rupture. In the method of the present invention, the positive internal pressure differential between intermediate compartment 16 and each of catholyte compartment 13 and anolyte compartment 10 typically has a minimum value of at least 0.07 Kilograms per square centimeter ($Kg/cm^2$) (1 pound per square inch (psi)), preferably at least 0.14 $Kg/cm^2$ (2 psi), and more preferably at least 0.21 $Kg/cm^2$ (3 psi). The positive internal pressure differential between intermediate compartment 16 and each of catholyte compartment 13 and anolyte compartment 10 will also typically have a maximum value of less than 1.40 $Kg/cm^2$ (20 psi), preferably less than 0.70 $Kg/cm^2$ (10 psi), and more preferably less than 0.49 $Kg/cm^2$ (7 psi). The positive internal pressure differential between intermediate compartment 16 and each of the catholyte compartment 13 and anolyte compartment 10 may range between any combination of the aforedescribed minimum and maximum values, inclusive of the recited values.

The present invention relates to a method of electrochemically preparing epoxides from α-halohydrin. As used herein and in the claims, by the term "α-halohydrin" is meant a hydroxy or polyhydroxy functional organic species having at least one halo group covalently bonded to an $Sp^3$ hybridized carbon atom, which is in a position alpha to at least one $Sp^3$ hybridized carbon atom having a hydroxy group covalently bonded thereto, e.g., 1-chloro-2-hydroxypropane and 1,3-dichloro-2-hydroxypropane. Further, as used herein and in the claims, by the term "epoxide" is meant an organic compound containing one or more three-membered cyclic ether groups, e.g., alkylene oxides and epihalohydrins.

The halo of the α-halohydrin is selected from the group consisting of chloro, bromo and iodo. The backbone of the α-halohydrin may be a straight or branched chain alkane having from 2 to 20 carbon atoms, preferably from 2 to 12 carbon atoms, and more preferably from 2 to 6 carbon atoms, e.g., ethane, propane, butane, isobutane, pentane, isopentane, hexane, octane, dodecane and octadecane, or a cyclic alkane having from 5 to 12 carbon atoms, e.g., cyclopentane, cyclohexane, cyclooctane and cyclododecane. Further, the α-halohydrin may have: aryl substituents, e.g., phenyl, cumenyl, mesityl, tolyl and xylyl substituents; ethylenic unsaturated substituents; and halogen, oxygen and sulfur-containing substituents, e.g., hydroxyl, thiol, carboxylic acid, ester, ether and thioether substituents.

The α-halohydrins useful in the present invention may be prepared by art-recognized methods, exemplary of which is the reaction of a hypohalous acid, e.g., hypochlorous acid, hypobromous acid or hypoiodous acid, with an olefin, e.g., ethene, propene, 1-butene, 2-butene, 1,3-butadiene, 9,10-octadecanoic acid, esters of 9,10-octadecanoic acid, 9,12-octadecadienoic acid, esters of 9,12-octadecadienoic acid, cyclopentene, vinylcyclopentane, cyclohexene, 1,4-cyclohexadiene, vinylcyclohexane, divinylcyclohexane, styrene and divinylbenzene. The reaction of hypohalous acid with an olefin will also typically result in the co-product formation of aqueous hydrogen halide, e.g., hydrogen chloride, hydrogen bromide or hydrogen iodide. The aqueous hydrogen halide co-product will generally be present in an amount of less than 3% by weight, for example, less than 2% by weight, based on the total weight of the aqueous solution comprising α-halohydrin.

Representative α-halohydrins useful in the present invention include, but are not limited to, 2-chloro-1-hydroxyethane, 2-bromo-1-hydroxyethane, 1-chloro-2-hydroxypropane, 1-iodo-2-hydroxypropane, 2-chloro-1-hydroxypropane, 1,3-dichloro-2-hydroxypropane, 2,3-dichloro-1-hydroxypropane, 1,3-dibromo-2-hydroxypropane, 2,3-dibromo-1-hydroxypropane, 3-chloro-1,2-dihydroxypropane, α-chlorohydroxybutane, e.g., 1-chloro-2-hydroxybutane, 1,4-dichloro-2,3-dihydroxybutane, 1-chloro-2-hydroxycyclopentane, (α-chloro-hydroxyethyl)cyclopentane, 1-chloro-2-hydroxycyclohexane, (α-chloro-hydroxyethyl)cyclohexane, bis(α-chloro-hydroxyethyl)cyclohexane, e.g., 1,2-, 1,3- and 1,4-bis(1-chloro-2-hydroxyethyl)cyclohexane, (α-chloro-hydroxyethyl)benzene and bis(α-chloro-hydroxyethyl) benzene, e.g., 1,2-, 1,3- and 1,4-bis(1-chloro-2-hydroxyethyl)benzene. In a preferred embodiment of the present invention, the α-halohydrin is selected from the group consisting of 1-chloro-2-hydroxypropane, 2-chloro-1-hydroxypropane, 1,3-dichloro-2-hydroxypropane, 1,3-dibromo-2-hydroxypropane and mixtures thereof.

When the α-halohydrin contains more than three carbon atoms, its solubility in the aqueous solution circulated through catholyte compartment 13 will be reduced and the rate at which it is converted to an epoxide will also be reduced. Accordingly, to improve the solubility of the α-halohydrin, a co-solvent may also be present in the circulated aqueous solution. Examples of cosolvents suitable for use in aqueous solutions include, but are not limited to: hydroxy functional ethers of ethylene glycol, e.g., butyl 2-hydroxyethyl ether and hexyl 2-hydroxyethyl ether; and hydroxy functional ethers of 1,2-dihydroxy propane, e.g., methyl 2-hydroxypropyl ether and phenyl 2-hydroxypropyl ether. If used, cosolvents are generally present in amounts of less than 10 percent by weight, e.g., less than 5 percent by weight, based on total weight of the aqueous solution circulated through catholyte compartment 13.

Representative epoxides that may be prepared in accordance with the method of the present invention include, but are not limited to, ethylene oxide, propylene oxide, 1-chloro-2,3-epoxypropane (epichlorohydrin), 1-bromo-2,3-epoxypropane (epibromohydrin), 1-hydroxy-2,3-epoxypropane, 1,2-epoxybutane, 2,3-epoxybutane, 1,2,3,4-diepoxybutane, 1,2-epoxypentane, 1,2-epoxyhexane, 1,2-epoxyoctane, 1,2,7,8-diepoxyoctane, 1,2-epoxydecane, 1,2-epoxydodecane, 6-oxabicyclo[3.1.0]hexane, 7-oxabicyclo[4.1.0]heptane, 3-epoxyethyl-7-oxabicyclo[4.1.0]heptane, 7-oxabicyclo[4.1.0]heptan-2-one, 3,4-epoxycyclohexylmethyl 3,4-epoxycyclohexanecarboxylate, exo-2,3-epoxynorborane, 9-oxabicyclo[6.1.0]nonane, 1,2,5,6-diepoxycyclooctane, 1,2-epoxycyclododecane, 1,2-epoxyethylbenzene, 2,3-(epoxypropyl)benzene, 1,2-epoxy-3-phenoxypropane and 2,3-epoxypropyl 4-methoxyphenyl ether.

The operation of electrolytic cells 9 and 2 of FIGS. 1–3 will now be described as they relate to preferred embodiments of the process of the present invention. An aqueous solution of α-halohydrin is circulated through catholyte compartment 13 by forwarding the solution from a source of a-halohydrin (not shown in FIGS. 1 and 2), e.g., temperature controlled reservoir 122 shown in FIG. 3, through a suitable conduit (shown by line 58) to catholyte compartment 13 through inlet 43; withdrawing a product stream comprising the epoxide and α-halohydrin from catholyte compartment 13 through outlet 46; and forwarding the withdrawn product stream by a suitable conduit (shown by line 61) to the source of α-halohydrin, e.g., reservoir 122.

The temperature of the aqueous solution of α-halohydrin will depend, for example, on its boiling point and the operating temperature limits of the anion exchange membrane 25. In the practice of the present invention, the aqueous solution of α-halohydrin is typically at a minimum temperature of at least 15° C., preferably at least 20° C., and more preferably at least 25° C. The aqueous solution of α-halohydrin is also typically at a maximum temperature of less than 40° C., preferably less than 35° C., and more preferably less than 30° C. The temperature of the aqueous solution of (α-halohydrin may range between any combination of these minimum and maximum temperature values, inclusive of the recited values.

The aqueous solution of α-halohydrin typically contains α-halohydrin in an amount of at least 1% by weight, preferably at least 2% by weight, and more preferably at least 3% by weight, based on the total weight of the aqueous solution comprising α-halohydrin. The (α-halohydrin is also typically present in an amount of not more than 30% by weight, preferably not more than 15% by weight, and more preferably not more than 10% by weight, based on the total weight of the aqueous solution of α-halohydrin. The amount of α-halohydrin present in the aqueous solution of α-halohydrin may range between any combination of these amounts, inclusive of the recited amounts.

Similarly and simultaneously with the circulation of the aqueous solution of (α-halohydrin through catholyte compartment 13, and in connection with electrolytic cell 2, a first aqueous solution of hydrogen halide is circulated through intermediate compartment 16. Circulation is accomplished by forwarding a solution of the first hydrogen halide solution from a source of the first hydrogen halide solution, e.g., temperature controlled reservoir 119 shown in FIG. 3, through a suitable conduit (shown by line 92) to intermediate compartment 16. A hydrogen halide process stream is withdrawn from intermediate compartment 16 through outlet 40 and forwarded through a suitable conduit or transfer line (shown by line 95) to the source of first aqueous solution of hydrogen halide, e.g., reservoir 119.

Contemporaneously and in a manner similar to the circulation of the respective process streams through each of the catholyte and intermediate compartments, a second aqueous solution of hydrogen halide is circulated through anolyte compartment 10. The second hydrogen halide aqueous solution is forwarded from a source thereof, e.g., temperature controlled reservoir 125 shown in FIG. 3, by means of a suitable conduit (shown by line 110) through liquid-gas separator 70 and then to catholyte compartment 10 through a suitable conduit (shown by line 113). The second hydrogen halide aqueous process stream is introduced into catholyte compartment 10 through inlet 32. A hydrogen halide process stream is withdrawn from anolyte compartment 10 through outlet 33 and forwarded to the source of second hydrogen halide solution, e.g., reservoir 125, through a suitable conduit (shown by line 128).

The temperature of each of the first and second aqueous solutions of hydrogen halide will depend on, for example, their respective boiling points and the operating temperature limits of the anion and cation exchange membranes. In the practice of the present invention the first and second aqueous solutions of hydrogen halide are each typically at a temperature of at least 25° C., preferably at least 30° C., and more preferably at least 40° C. The first and second aqueous solutions of hydrogen halide are each also typically at a temperature of less than 70° C., preferably less than 65° C., and more preferably less than 60° C. The temperature of the first and second aqueous solutions of hydrogen halide may each range between any of these temperatures, inclusive of the recited temperature values.

The halide of the first and second aqueous solutions of hydrogen halide, is preferably the same as that of the α-halohydrin, e.g., chloride. In the method of the present invention, each of the first and second aqueous solutions of hydrogen halide typically has a hydrogen halide concentration of at least 1% by weight, preferably at least 5% by weight, and more preferably at least 10% by weight, based on the total weight of each of said first and second aqueous solutions of hydrogen halide, respectively. The concentration of hydrogen halide in each of the first and second aqueous solutions of hydrogen halide is also typically less than 25% by weight, preferably less than 20% by weight, and more preferably less than 15% by weight, based on the total weight of each of the first and second aqueous solutions of hydrogen halide, respectively. The concentration of hydrogen halide present in each of the first and second aqueous solutions of hydrogen halide may range between any of these values, inclusive of the recited values. In a preferred embodiment of the present invention, the first and second aqueous solutions of hydrogen halide are each comprised of an aqueous solution of hydrogen chloride.

Electrolytic cells 9 and 2 may be operated at a current density of at least 0.05 Kiloamperes per square meter of electrode surface available for electrochemical reaction (Kamps/m$^2$), preferably at least 0.1 Kamps/m$^2$, and more preferably at least 0.2 Kamps/m$^2$. The current density also should not be more than 10 Kamps/m$^2$, preferably not more than 7 Kamps/m$^2$, and more preferably not more than 6 Kamps/m$^2$ In the practice of the method of the present invention, the current density may range between any combination of these values, inclusive of the recited values. The surface area of the electrode being here calculated from its perimeter dimensions alone.

Although not meaning to be bound by any theory, it is believed from the evidence at hand that the current passing through electrolytic cells 9 and 2 results in the following chemical and electrochemical reactions. The electrochemical and chemical reactions believed to occur within catholyte compartment 13 may be represented by the following General Scheme I:

General Scheme I

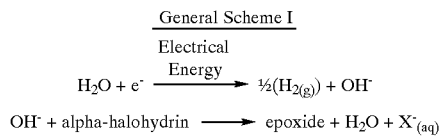

wherein, X$^-$ represents halide anion. Halide anions X$^-$ are selectively transported across anion exchange membrane 25 and pass into intermediate compartment 16. The electrons consumed, as shown in General Scheme I, are provided by cathode 28. Hydrogen gas generated within catholyte compartment 13 is forwarded along with the circulating α-halohydrin/epoxide process stream through conduit 61 to reservoir 122 from where it may be recovered through a gas discharge conduit (shown by line 131).

Within anolyte compartment 10, the following electrochemical reaction is believed to occur, as represented by General Scheme II:

General Scheme II

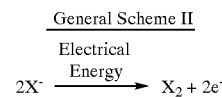

The source of halide anions (X$^-$) is the second aqueous solution of hydrogen halide circulating through anolyte compartment 10, in the case of electrolytic cell 2. In the case of electrolytic cell 9, the source of halide anions is the aqueous solution of hydrogen halide circulating through both of the intermediate and anolyte compartments. The oxidation of two moles of halide anion to one mole of diatomic halogen (X$_2$), will leave a balance of two moles of hydrogen cation in solution, which are selectively transported across cation exchange membrane 22 into intermediate compartment 16. Diatomic halogen generated within anolyte compartment 10 is forwarded along with the circulating second aqueous hydrogen halide process stream to liquid-gas separator 70 from where it may be recovered through gas discharge conduit 67.

Within intermediate compartment 16, halide anions transported across anion exchange membrane 25 from catholyte compartment 13, and hydrogen cations transported across cation exchange membrane 22 from anolyte compartment 10 together form aqueous hydrogen halide, e.g., aqueous hydrogen chloride. During the operation of electrolytic cell 2, the concentration of aqueous hydrogen halide within intermediate compartment 16 will increase, and correspondingly, the concentration of aqueous hydrogen halide within anolyte compartment 10 will decrease. The accumulation of hydrogen halide in intermediate compartment 16 and its depletion within anolyte compartment 10 will result in a decrease in the operating efficiency of electrolytic cell 2. Examples of degraded operating efficiency include, higher required operating cell potentials and reduced current efficiency resulting from the back migration of protons and halide anions across the ion exchange membranes.

The operating efficiency of the electrolytic cell used in the present invention may be maintained at an optimum level by either (a) introducing a portion of the first hydrogen halide process stream circulating through intermediate compartment 16 into anode compartment 10, e.g., the embodiment represented by FIG. 3, or (b) circulating a single aqueous solution of hydrogen halide through both the intermediate and anolyte compartments, e.g., the embodiments represented by FIGS. 1 and 2. With reference to FIG. 3, a portion, e.g., a bleed or side stream, of the first aqueous hydrogen halide process stream passing through conduit 92 is forwarded through a suitable conduit (represented by line 98) through valve 107 and introduced into reservoir 125 by means of a suitable conduit (represented by line 99). The combination of said portion of the first hydrogen halide process stream introduced into reservoir 125 through conduit 99 and the circulating second aqueous hydrogen halide stream removed from anolyte compartment 10 is forwarded through conduit 110 to liquid-gas separator 70 and from there to anolyte compartment 10 by means of conduit 113.

Valve 107 is used to control the amount of the side stream of the first hydrogen halide process stream charged to reservoir 125. Valve 107 can be adjusted manually or remotely in response to a feed-back control loop, not shown, in which, for example, the pH of the intermediate and anolyte compartments are continually measured and compared. Measurements of the charge consumed by electrolytic cell 2 may be used to determine, e.g., through calculation using the Faraday equation, the amount of hydrogen halide consumed in anolyte compartment 10 and accumulated in intermediate compartment 16, valve 107 being then adjusted accordingly in response to such determination.

FIGS. 1 and 2 represent two further embodiments of the present invention in which the operating efficiency of electrolytic cell 9 is maintained at an optimum level, relative to the accumulation of hydrogen halide in intermediate compartment 16 and its depletion in anolyte compartment 10. As represented in FIGS. 1 and 2, a single aqueous solution of hydrogen halide is circulated through both the intermediate and anolyte compartments by: forwarding an aqueous solution of hydrogen halide from a source of hydrogen halide, e.g., temperature controlled reservoir 73, through a suitable conduit (shown by line 55) to intermediate compartment 16; withdrawing a hydrogen halide process stream from intermediate compartment 16 through outlet 40; forwarding withdrawn hydrogen halide in sequence through a suitable conduit (shown by line 52), valve 83 and another suitable conduit (shown by line 53) to anolyte compartment 10. Aqueous hydrogen halide is withdrawn from anolyte compartment 10 through outlet 31 and returned to the aqueous hydrogen halide source, e.g., reservoir 73, through a suitable conduit (shown by line 49).

The method of the present invention includes minimizing substantially the presence of diatomic halogen, e.g. chlorine ($Cl_2$), and hypohalous acid, e.g., hypochlorous acid (HOCl), within intermediate compartment 16. As described previously, diatomic halogen is generated within anolyte compartment 10. In an aqueous environment, diatomic halogen, e.g., diatomic chlorine, can form hypohalous acid, e.g., hypochlorous acid. The presence of diatomic halogen and/or hypohalous acid within intermediate compartment 16 can result in degradation of anion exchange membrane 25.

As used herein the term "minimizing substantially" is meant to refer to a method(s) of controlling the amount of diatomic halogen and/or hypohalous acid present within intermediate compartment 16 at levels that will not adversely affect, i.e., degrade, anion exchange membrane 25. In accordance with the present invention, it is preferred that the concentration of diatomic halogen and/or hypohalous acid within intermediate compartment 16 be not more than 1 part per million parts of the aqueous solution in compartment 16 (1 ppm), preferably not more than 0.5 ppm, more preferably not more than 0.1 ppm.

In the embodiment of the present invention represented by FIG. 3, the presence of diatomic halogen and/or hypohalous acid within intermediate compartment 16 is minimized primarily by the arrangement of the process streams around each of the intermediate and anolyte compartments. The process streams are arranged such that the second hydrogen halide process stream removed from anolyte compartment 10, which contains diatomic halogen and hypohalous acid, is not introduced directly into intermediate compartment 16.

While the diatomic halogen and hypohalous acid generated within anolyte compartment 10, in the embodiment represented by FIG. 3, are not introduced directly into intermediate compartment 16, it is possible that they may enter intermediate compartment 16 by diffusion across cation exchange membrane 22. To ensure that the presence of these materials within intermediate compartment 16 is substantially minimized, a diatomic halogen and hypohalous acid eliminating reagent, may be introduced into the liquid process stream circulating through intermediate compartment 16 or directly into intermediate compartment 16. The term "diatomic halogen and hypohalous acid eliminating reagent" as used herein refers to a reagent or mixture of reagents that will react with and effectively eliminate those materials from the circulating process stream. This reagent is preferably an aqueous solution of an alkaline reagent that neutralizes diatomic halogen and/or hypohalous acid and that is compatible, i.e., not harmful, with the components of the electrolytic cell that the alkaline reagent contacts. For example, the alkaline reagent preferably comprises a member selected from the group consisting of alkali metal hydrosulfide, alkali metal thiosulfate and mixtures thereof. In a particularly preferred embodiment of the present invention, the alkali metal of the alkali metal hydrosulfide and alkali metal thiosulfate is sodium.

In the embodiment of the present invention represented by FIG. 3, the diatomic halogen and/or hypohalous acid eliminating reagent is introduced into the liquid process stream circulating through intermediate compartment 16 by introducing the reagent into reservoir 119 through a suitable conduit (shown by line 116). The aforedescribed reagent mixes with the first hydrogen halide process stream removed from intermediate compartment 16 and reacts with any diatomic halogen and/or hypohalous acid present therein. In addition, any residual unreacted eliminating reagent present in the process stream is forwarded from reservoir 119 through conduit 92 to intermediate compartment 16.

In the embodiment of the present invention represented by FIGS. 1 and 2, the hydrogen halide process stream removed from anolyte compartment 10 is introduced indirectly into intermediate compartment 16. To minimize substantially the presence of diatomic halogen and hypohalous acid within intermediate compartment 16, the diatomic halogen and hypohalous eliminating reagent described above is introduced into the liquid process stream circulating through both of the intermediate and anolyte compartments. As shown in FIG. 1, the reagent is forwarded through a suitable conduit (shown by line 89), from a source not shown, into reservoir 73 wherein it mixes with the hydrogen halide process stream removed from anolyte compartment 10 and reacts with and eliminates any diatomic halide and hypohalous acid therein. The resultant mixture is removed from reservoir 73 through a suitable conduit (shown by line 55) and forwarded to intermediate compartment 16 by means of conduit 55. While the reagent may be introduced into the circulating liquid around the intermediate and anolyte compartments at any convenient point, it is preferred that it be introduced at a point in the circulating liquid between outlet 31 and inlet 37.

The diatomic halogen and hypohalous acid eliminating reagent is introduced into the appropriate circulating liquid process stream in an amount sufficient to substantially minimize the presence of these materials within intermediate compartment 16. This sufficient amount of reagent can be determined, for example, empirically through experimentation or by calculation of the amount of diatomic halogen formed within the anolyte compartment 10, e.g., using the Faraday equation.

In the embodiment of the present invention represented by FIG. 1, the reagent is introduced into the liquid process stream circulating through both of the intermediate and anolyte compartments in an amount at least equivalent to the amount of diatomic halogen being generated within anolyte compartment 10, i.e., a stoichiometric amount. It is preferred that the reagent be added in an amount that is slightly in excess of this stoichiometric amount, e.g., an amount that is 1% to 5% by equivalents, based on total equivalents, in excess of the stoichiometric amount.

In the embodiment of the present invention represented by FIG. 2, the diatomic halogen and hypohalous eliminating reagent is introduced into the liquid stream circulating through both of the intermediate and anolyte compartments in an amount that is typically less than equivalent to the amount of diatomic halogen generated in anolyte compartment 10, i.e., less than a stoichiometric amount. In FIG. 2, at least a portion of the diatomic halogen generated within anolyte compartment 10 is removed from the circulating liquid stream by passage through liquid-gas separator 70, as described below, and as a result is not forwarded into intermediate compartment 16.

With reference to the embodiment of the present invention represented by FIG. 3, the alkaline reagent is introduced into the process stream removed from intermediate compartment 16 in an amount that is typically less than equivalent to the amount of diatomic halogen generated in anolyte compartment 10. Due principally to the arrangement of process streams around the intermediate and anolyte compartments, as represented in FIG. 3, if diatomic halogen and hypohalous acid enters intermediate compartment 16 it does so typically by diffusion across cation exchange membrane 22. Such diffusion results in concentrations of diatomic halogen and hypohalous acid within intermediate compartment 16 of, e.g., less than 1 ppm.

To further ensure that the presence of diatomic halogen and hypohalous acid within intermediate compartment 16 of electrolyte cell 9 is substantially minimized in the embodiment of FIG. 2, a liquid-gas separator 70 may be included in the loop between outlet 31 of anolyte compartment 10 and inlet 37 of intermediate compartment 16. Liquid-gas separator 70 is used to remove gaseous diatomic halogen generated within anolyte compartment 10 from the circulating hydrogen halide process stream. With reference to FIG. 2, hydrogen halide process stream removed from anolyte compartment 10 is introduced into liquid-gas separator 70 through a suitable conduit (shown by line 49); gaseous diatomic halogen is removed from liquid-gas separator 70 through a suitable conduit (shown by line 67), and the resultant hydrogen halide process stream is introduced into reservoir 73 through a suitable conduit (shown by line 64).

The gaseous diatomic halogen removed from the liquid-gas separator 70 through conduit 67 may be passed through a condenser, not shown, and collected as concentrated diatomic halogen. Liquid-gas separators are known to those skilled in the art, and depending on the application can be operated under conditions that enhance the separation of gases from liquids, e.g., elevated temperatures and/or reduced pressures.

During the operation of electrolytic cells 9 and 2, water may diffuse across anion exchange membrane 25, resulting in an increase in the amount of water in the process stream circulating through intermediate compartment 16. Depending on the amount of water in the circulating stream and the amount of alkaline reagent added thereto, it may be necessary to reduce the volume of the process stream circulating through intermediate compartment 16 either periodically or continuously. With reference to FIGS. 1 and 2, this volume correction can be accomplished by withdrawing an appropriate amount of the circulating hydrogen halide process stream through valve 83, i.e., a bleed stream, and removing this bleed stream through an appropriate conduit (shown by line 86). With reference to FIG. 3, the volume correction can be accomplished similarly at any convenient point in the closed loop around intermediate compartment 16, preferably at a point in conduit 95, not shown.

The practice of the method of the present invention includes the step of removing an aqueous solution comprising epoxide, e.g., alkylene oxide, from compartment 13, and forwarding this process stream through conduit 61. The process stream withdrawn from compartment 13 will contain a higher amount of epoxide than the process stream entering compartment 13.

When the concentration of epoxide, e.g., alkylene oxide, in the process stream circulating through catholyte compartment 13 reaches a desired level, the epoxide is recovered from that stream. of the total molar equivalents of $\alpha$-halohydrin initially present in the aqueous solution of ($\alpha$-halohydrin circulated through compartment 13, at least 50% preferably at least 80% more preferably at least 99%, and particularly preferably 100% of these equivalents are converted to epoxide in accordance with the practice of the method of the present invention.

Epoxide, e.g., alkylene oxide, produced according to the present invention may be recovered, i.e., isolated, from the aqueous solution removed from compartment 13 by methods that are known to those of ordinary skill in the art. Such art-recognized recovery methods include, but are not limited to, steam distillation and vacuum distillation.

While a batch process has been described, a continuous process for converting the $\alpha$-halohydrin to epoxide is contemplated. For example, a side stream of the circulating aqueous stream of $\alpha$-halohydrin can be removed to make the process a continuous or semi-continuous process.

While FIGS. 1–3 depict singular representations of electrolytic cells, it should be understood that the scope of the present invention is also inclusive of the utilization of a plurality of such cells. The present invention may be practiced using a plurality of cells, e.g., electrolytic cells 9 or 2, either in series or parallel. In one embodiment, a plurality of cells, not shown, e.g., electrolytic cell 2, are utilized in series, wherein the outlets 46, 40 and 33 of each preceding cell are in respective liquid communication with the inlets 43, 37 and 32 of each succeeding cell by means of additional conduits, not shown.

In another embodiment of the present invention, a plurality of cells, not shown, e.g., electrolytic cell 2, are utilized in parallel, wherein, for example, inlet 43 and outlet 46 of catholyte compartment 13 of each cell are in common closed loop liquid communication with reservoir 122 by means of conduits and manifolds, not shown. Accordingly, the inlets and outlets of intermediate compartment 16 and anolyte compartment 10 of each cell are in common closed loop liquid communication with reservoir 119 and reservoir 125 respectively, by means of conduits and manifolds, not shown.

The present invention has been described with reference to specific details of particular embodiments thereof. It is not intended that such details be regarded as limitations upon the scope of the invention except insofar as and to the extent that they are included in the accompanying claims.

We claim:

1. A method of converting α-halohydrin to epoxide comprising:
   (a) providing an electrolytic cell having a catholyte compartment containing a cathode assembly, an anolyte compartment containing an anode assembly, and an intermediate compartment separating said catholyte and anolyte compartments;
   (b) introducing an aqueous solution of (α-halohydrin into said catholyte compartment;
   (c) introducing a first aqueous solution comprising hydrogen halide into said intermediate compartment;
   (d) introducing a second aqueous solution comprising hydrogen halide into said anolyte compartment;
   (e) passing direct current through said electrolytic cell; and
   (f) removing an aqueous solution comprising epoxide from said catholyte compartment, said cathode assembly comprising a cathode and an anion exchange membrane, said anode assembly comprising a cation exchange membrane and an anode, and said intermediate compartment being partitioned from said catholyte and anolyte compartments respectively by said anion exchange membrane and said cation exchange membrane.

2. The method of claim 1 wherein said α-halohydrin is selected from the group consisting of 2-chloro-1-hydroxyethane, 1-chloro-2-hydroxypropane, 2-chloro-1-hydroxypropane, 1,3-dichloro-2-hydroxypropane, 1,3-dibromo-2-hydroxypropane, 1-chloro-2-hydroxycyclopentane, 1-chloro-2-hydroxycyclohexane, (α-chloro-hydroxyethyl)cyclohexane, bis(α-chloro-hydroxyethyl)cyclohexane, (α-chloro-hydroxyethyl)benzene, bis(α-chloro-hydroxyethyl)benzene and mixtures thereof.

3. The method of claim 2 wherein said α-halohydrin is selected from the group consisting of 1-chloro-2-hydroxypropane, 2-chloro-1-hydroxypropane, 1,3-dichloro-2-hydroxypropane, 1,3-dibromo-2-hydroxypropane and mixtures thereof.

4. The method of claim 1 wherein each of said first and second hydrogen halide aqueous solutions has a concentration of from 1% by weight to 25% by weight hydrogen halide, based on the total weight of each of said first and second hydrogen halide aqueous solutions respectively.

5. The method of claim 1 further comprising introducing a portion of hydrogen halide process stream removed from said intermediate compartment into said anolyte compartment.

6. The method of claim 1 further comprising introducing an alkaline reagent into hydrogen halide process stream removed from said intermediate compartment to form a mixture, and introducing said mixture into said intermediate compartment.

7. The method of claim 6 wherein said alkaline reagent is an aqueous solution comprising a member selected from the group consisting of alkali metal hydrosulfide, alkali metal thiosulfate and mixtures thereof.

8. The method of claim 1 wherein said anion exchange membrane comprises a copolymer of styrene and divinylbenzene having pendent quaternary ammonium salt groups, said cation exchange membrane comprises a perfluoropolymer having pendent sulfonic acid groups, said cathode comprises a material selected from the group consisting of graphite, platinum, titanium coated with platinum, titanium coated with an oxide of ruthenium, nickel, stainless steel, high alloy steel and appropriate combinations of such materials, and said anode comprises titanium coated with an oxide of ruthenium.

9. The method of claim 1 wherein a positive internal pressure differential of from 0.07 kg/cm$^2$ to 1.40 kg/cm$^2$ exists between said intermediate compartment and each of said catholyte compartment and anolyte compartment.

10. A method of converting α-halohydrin to epoxide comprising:
    (a) providing an electrolytic cell having a catholyte compartment containing a cathode assembly, an anolyte compartment containing an anode assembly, and an intermediate compartment separating said catholyte and anolyte compartments;
    (b) introducing an aqueous solution of (α-halohydrin into said catholyte compartment;
    (c) circulating an aqueous solution comprising hydrogen halide through both of said anolyte and said intermediate compartments;
    (d) passing direct current through said electrolytic cell; and
    (e) removing an aqueous solution comprising epoxide from said catholyte compartment, said cathode assembly comprising a cathode and an anion exchange membrane, said anode assembly comprising a cation exchange membrane and an anode, and said intermediate compartment being partitioned from said catholyte and anolyte compartments respectively by said anion exchange membrane and said cation exchange membrane.

11. The method of claim 10 wherein said α-halohydrin is selected from the group consisting of 2-chloro-1-hydroxyethane, 1-chloro-2-hydroxypropane, 2-chloro-1-hydroxypropane, 1,3-dichloro-2-hydroxypropane, 1,3-dibromo-2-hydroxypropane, 1-chloro-2-hydroxycyclopentane, 1-chloro-2-hydroxycyclohexane, (α-chloro-hydroxyethyl)cyclohexane, bis((α-chloro-hydroxyethyl)cyclohexane, (α-chloro-hydroxyethyl)benzene, bis(α-chloro-hydroxyethyl)benzene and mixtures thereof.

12. The method of claim 11 wherein said α-halohydrin is selected from the group consisting of 1-chloro-2- hydroxypropane, 2-chloro-1-hydroxypropane, 1,3-dichloro-2-hydroxypropane, 1,3-dibromo-2-hydroxypropane and mixtures thereof.

13. The method of claim 10 wherein said hydrogen halide aqueous solution has a concentration of from 1% by weight to 25% by weight hydrogen halide, based on the total weight of said hydrogen halide aqueous solutions respectively.

14. The method of claim 13 further comprising treating hydrogen halide process stream removed from said anolyte compartment with an alkaline reagent, and recycling the resultant mixture into said intermediate compartment.

15. The method of claim 14 wherein said alkaline reagent is an aqueous solution comprising a member selected from the group consisting of alkali metal hydrosulfide, alkali metal thiosulfate and mixtures thereof.

16. The method of claim 15 further comprising passing hydrogen halide process stream removed from said anolyte compartment through a liquid-gas separator, said process stream containing diatomic halogen, and removing diatomic halogen from said liquid-gas separator.

17. The method of claim 10 wherein said anion exchange membrane comprises a copolymer of styrene and divinylbenzene having pendent quaternary ammonium salt groups, said cation exchange membrane comprises a perfluoropolymer having pendent sulfonic acid groups, said cathode comprises a material selected from the group consisting of graphite, platinum, titanium coated with platinum, titanium coated with an oxide of ruthenium, nickel, stainless steel, high alloy steel and combinations of such materials, and said anode comprises titanium coated with an oxide of ruthenium.

18. The method of claim 10 wherein a positive internal pressure differential of from 0.07 kg/cm$^2$ to 1.40 kg/cm$^2$ exists between said intermediate compartment and each of said catholyte compartment and anolyte compartment.

* * * * *